(12) United States Patent
Wang et al.

(10) Patent No.: US 6,699,992 B2
(45) Date of Patent: Mar. 2, 2004

(54) PROCESS FOR PREPARING QUINOLONECARBOXYLIC ACIDS

(75) Inventors: Yuncai Wang, Dalian (CN); Rongye Chen, Dalian (CN); Haijun Nan, Dalian (CN)

(73) Assignee: Lynchem Co., Ltd., Dalian (CN)

( * ) Notice: Subject to any disclaimer, the term of this patent is extended or adjusted under 35 U.S.C. 154(b) by 25 days.

(21) Appl. No.: 10/344,643

(22) PCT Filed: Jul. 6, 2001

(86) PCT No.: PCT/CN01/01156
§ 371 (c)(1),
(2), (4) Date: Feb. 12, 2003

(87) PCT Pub. No.: WO02/059094
PCT Pub. Date: Aug. 1, 2002

(65) Prior Publication Data
US 2003/0166936 A1 Sep. 4, 2003

(30) Foreign Application Priority Data
Aug. 16, 2000 (CN) .......................... 00123446 A

(51) Int. Cl.$^7$ ............................. C07D 215/56
(52) U.S. Cl. ....................... 546/156; 546/155
(58) Field of Search ................. 546/155, 156

(56) References Cited
U.S. PATENT DOCUMENTS
4,730,000 A * 3/1988 Chu ........................ 514/254

* cited by examiner

Primary Examiner—Patricia L. Morris
(74) Attorney, Agent, or Firm—McAndrews, Held & Malloy, Ltd.

(57) ABSTRACT

The present invention provides a process for preparing quinolonecarboxylic acid derivatives having the formula (I):

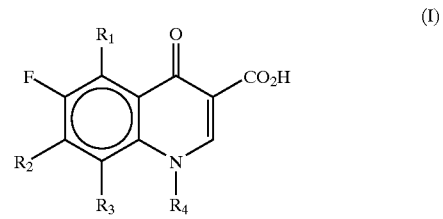

(I)

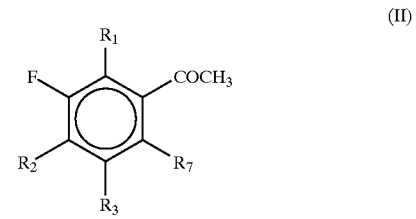

(II)

wherein $R_1$ is H, halogen, or amino; $R_2$ is halogen; $R_3$ is H, halogen, $C_{1-4}$ alkoxyl, or CN; $R_4$ is selected from the group consisting of $C_{3-6}$cycloalkyl, $C_{1-4}$alkyl, $C_{1-4}$alkoxy$C_{1-4}$alkyl, and $C_{1-4}$alkylamino$C_{1-4}$alkyl. The invention also provides new acetophenones having the formula (II) that are intermediates for preparing the compound of the formula (I).

5 Claims, No Drawings

PROCESS FOR PREPARING QUINOLONECARBOXYLIC ACIDS

FIELD OF THE INVENTION

The present invention relates to a process for preparing quinolonecarboxylic acids, particularly to a process for preparing quinolonecarboxylic acids from acetylbenzene polyhalides.

BACKGROUND OF THE INVENTION

People have increasingly paid attention to anti-infection drugs of quinolones due to their excellent properties. Quinolonecarboxylic acids are key intermediates of the anti-infection drugs since all the drugs of quinolones are based on such intermediates followed by a series of reactions. Therefore, the synthesis of the intermediates of quinolonecarboxylic acids is very important in the preparation of the quinolone drugs.

Various methods of preparing quinolonecarboxylic acids have been disclosed in the prior art. For example, Gaticarboxylic acid is prepared starting from 2,4,5-trifluoro-3-methoxylbenzene carboxylic acid, and Sparcarboxylic acid is prepared starting from pentafluorobenzenecarboxylic acid. However, the yield of the subject compound in these methods is not satisfied. The invention is hereby provided to overcome the drawbacks.

SUMMARY OF THE INVENTION

One object of the invention is to provide a new process for preparing quinolonecarboxylic acid derivatives starting from acetylbenzene polyhalides. The process according to the invention has fewer steps but a higher yield to obtain the subject compound.

According to the present invention, the process for preparing quinolonecarboxylic acid derivatives having the formula (I):

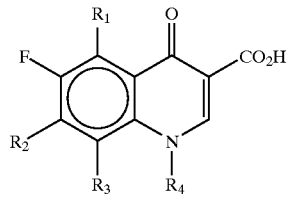
(I)

wherein $R_1$ is H, halogen, or amino,
$R_2$ is halogen,
$R_3$ is H, halogen, $C_{1-4}$alkoxyl, or CN,
$R_4$ is selected from the group consisting of $C_{3-6}$cycloalkyl, $C_{1-4}$alkyl, $C_{1-4}$alkoxyl$C_{1-4}$alkyl, and $C_{1-4}$alkylamino$C_{1-4}$alkyl,
comprising the steps of:
i) reacting a compound of the formula (II)

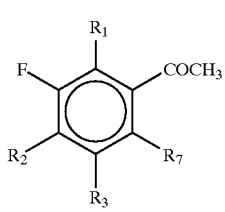
(II)

wherein $R_1$, $R_2$ and $R_3$ are defined as above, and $R_7$ is a halogen, with an alkyl carbonate to obtain a compound of the formula (III),

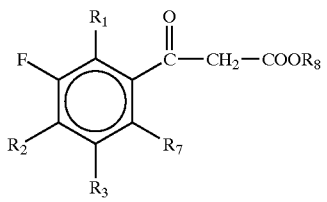
(III)

wherein $R_8$ is methyl or ethyl;
ii) reacting a compound of the formula (III) successively with an alkyl orthoformate and a compound of the formula (IV) $R_4NH_2$ to obtain a compound of the formula (V),

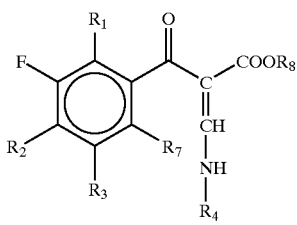
(V)

iii) cyclizing the compound of the formula (V) in the presence of a base to form a compound of the formula (VI); and

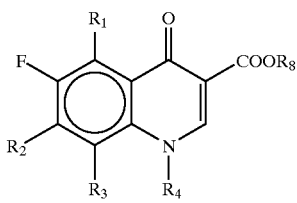
(VI)

iv) hydrolyzing the compound of the formula (VI) to obtain a compound of the formula (I).

The another object of the invention is to provide some compounds having the formula (II),

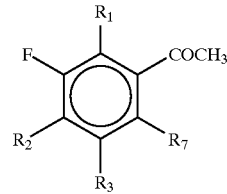
(II)

In the formula (II), those compounds, in which $R_1$ is H, or Cl; $R_2$ is Cl; $R_3$ is F, $C_{1-4}$ alkoxy, or CN; and $R_7$ is Cl, are novel compounds.

DETAILED DESCRIPTION OF THE INVENTION

In the process for preparing compounds of the formula (I) according to the present invention, $R_1$ is preferably H, F, or $NH_2$; $R_2$ is preferably F or Cl; $R_3$ is preferably F, CN or $CH_3$; and $R_4$ is preferably cyclopropyl or cyclohexyl.

Methyl carbonate or ethyl carbonate can be used in the reaction with compounds having the formula (II). This reaction in general is carried out in the presence of a base in organic solvents. Preferably, carbonates themselves are used as reaction solvents. The base used herein may be NaH or sodium alkoxide.

In general, the reaction between compounds of the formula (III) and orthoformates may be carried out in the presence of diacetyl oxide, and the resultant may be directly reacted with $R_4NH_2$ of the formula (IV) to obtain a compound having the formula (V).

Cyclization of the compound of the formula (V) can be carried out in an organic solvent in the presence of a base to obtain a compound having the formula (VI). Preferable solvent is DMF, and anhydrous sodium carbonate may be selected as the base.

The compound of the formula (VI) can be hydrolyzed to give the corresponding compound of the formula (I) using a conventional method in the art.

In the process of the present invention, the compound of the formula (I) in which $R_1$ is $NH_2$ can be converted from a compound thereof in which $R_1$ is halogen. The reaction scheme is shown as follows:

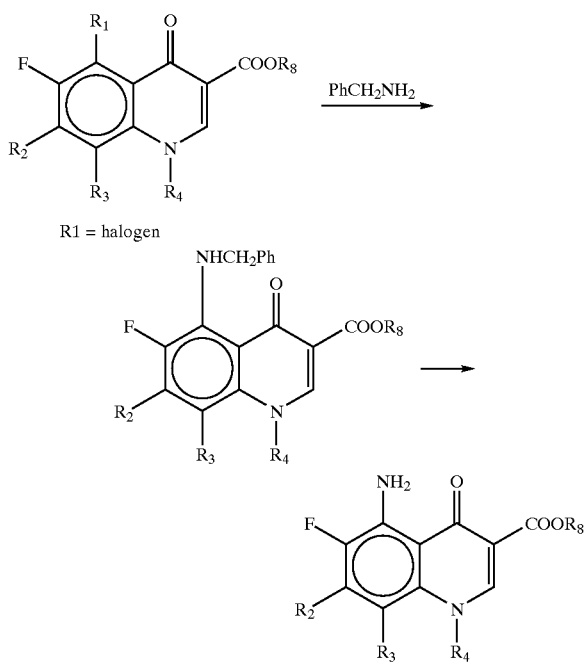

In the compound of the formula (II), $R_1$ is preferably H, and $R_3$ is preferably F, $OCH_3$ or CN.

Although the compound having the formula (II) can be prepared by many methods in the art, it is prepared in the invention starting from benzene polyhalides that can be easily obtained commercially.

The invention will be further illustrated with the following examples.
Preparation of Quinolonecarboxylic Acids

EXAMPLE 1
Gaticarboxylic Acids Prepared From 2,4-Dichloro-5-fluoro-3-methoxyacetylbenzene
Methyl 2,4-Dichloro-5-fluoro-3-methoxybenzoylacetate 80.6 g of 2,4-dichloro-5-fluoro-3-methoxyacetylbenzene (0.34 mol) in 1000 ml of dimethyl carbonate was stirred. 50 g of 50% NaH (1.04 mol) was added in batch to the resulting solution at ambient temperature. After the addition, the reaction was carried out at 80° C. for 3 hours. The reactant was then poured into ice water containing a little amount of acetate acid. The resulting mixture was extracted with ethyl ether. The extract was washed with water, dried over anhydrous sodium sulfate. The residue was recrystallized from methanol after ethyl ether was evaporated and excessive dimethyl carbonate was recovered from the solution, thereby to afford 80.8 g of methyl 2,4-dichloro-5-fluoro-3-methoxybenzoylacetate (0.274 mol) in 80.6% yield having a melt point of 50–53° C.
Methyl 2-(2,4-Dichloro-5-fluoro-3-methoxybenzoyl)-3-cyclopropylaminoacrylate 73.8 g of methyl 2,4-dichloro-5-fluoro-3-methoxybenzoylacetate (0.25 mol), 66.6 g of triethyl orthoformate (0.45 mol) and 77.4 g of diacetyl oxide (0.72 mol) were stirred at 150° C. for 2.5 hours. Fractions having a lower boiling point were evaporated under reduced pressure. To the residue was added 250 ml of anhydrous ethanol. 14.5 g of cyclopropylamine (0.25 mol) was added to the solution and the reaction was then carried out for 2 hours. The resulting mixture was filtered under suction. The residue was re-crystallized from a mixture of petroleum ether and cyclohexane to yield 66.0 g (0.182 mol) of methyl 2-(2,4-dichloro-5-fluoro-3-methoxybenzoyl)-3-cyclopropylaminoacrylate in 72.9% yield.
Methyl 1-Cyclopropyl-7-chloro-6-fluoro-8-methoxy-1,4-dihydro-4-oxo-3-quinoline-carboxylate 34.7 g of anhydrous $K_2CO_3$ (0.35 mol) was added to a solution of 62.6 g of methyl 2-(2,4-dichloro-5-fluoro-3-methoxybenzoyl)-3-cyclopropylaminoacrylate in 220 ml of DMF. The reactant was stirred at 40–45° C. for 2.5 hours, and the reaction was monitored by TLC. The resulting mixture was then poured into 800 ml of ice-water, filtered, washed with water (100 ml×2), and dried. The resulting solid was dissolved in 120 ml of 95% methanol and then refluxed for 15 minutes, cooled, filtered and dried to afford 50.8 g of methyl 1-cyclopropyl-7-chloro-6-fluoro-8-methoxy-1,4-dihydro-4-oxo-3-quinolinecarboxylate (0.156 mol) as a white solid, mp 184–187C., in 90.1% yield.
1-Cyclopropyl-7-chloro-6-fluoro-8-methoxy-1,4-dihydro-4-oxo-3-quinoline-carboxylic Acid 28.6 g of methyl 1-cyclopropyl-7-chloro-6-fluoro-8-methoxy-1,4-dihydro-4-oxo-3-quinolinecarboxylate (0.088 mol), 160 ml of acetate acid, 100 ml of water and 18 ml of concentrated sulfuric acid were stirred for 40 minutes at 100–110° C. The resulting mixture was cooled and filtered. The precipitate was re-crystallized from choroform-ethanol to afford 25.2 g of 1-cyclopropyl-7-chloro-6-fluoro-8-methoxy-1,4-dihydro-4-oxo-3-quinolinecarboxylic acid (Gaticarboxylic acid, 0.081 mol) in 91.8% yield, mp 195–199° C.

EXAMPLE 2
8-Cyano-quinolonecarboxylic Acid from 3-cyano-2,4-dichloro-5-fluoroacetylbenzene
Ethyl 3-Cyano-2,4-dichloro-5-fluorobenzyolacetate 78.9 g of 3-cyano-2,4-dichloro-5-fluoroacetylbenzene (0.34 mol) in 1000 ml of diethyl carbonate was stirred. To the solution was added in batch 50.0 g of 50% NaH (1.04 mol) at room temperature. The reaction was carried out at 80° C. for 3 hours. The resultant was carefully poured into ice-water containing a little mount of acetate acid, extracted with ethyl ether. The extract was washed with water, dried over anhydrous sodium sulfate. The residue was recrystallized from toluene after ethyl ether was evaporated and excessive dimethyl carbonate was recovered from the solution to afford 86.6 g of ethyl 3-cyano-2,4-dichloro-5-fluorobenzoylacetate (0.285 mol) in 83.7% yield.

Ethyl 2-(3-Cyano-2,4-dichloro-5-fluorobenzoyl)-3-cyclopropylaminoacrylate 76.0 g of ethyl 3-cyano-2,4-dichloro-5-fluorobenzoylacetate (0.25 mol), 66.6 g of triethyl orthoformate (0.45 mol) and 77.4 g of diacetyl oxide (0.72 mol) were stirred at 150° C. for 2.5 hours. Fractions having a lower boiling point were evaporated under reduced pressure. To the residue was added 250 ml of anhydrous ethanol. 14.5 g of cyclopropylamine (0.25 mol) was added to the solution and the reaction was then carried out for 2 hours. The resulting mixture was filtered under suction. The residue was recrystallized from a mixture of petroleum ether and cyclohexane to yield 65.0 g (0.175 mol) of ethyl 2-(3-cyano-2,4-dichloro-5-fluorobenzoyl)-3-cyclopropylaminoacrylate in 70.1% yield.

Ethyl 8-Cyano-1-cyclopropyl-7-chloro-6-fluoro-1,4-dihydro-4-oxo-3-quinolinecarboxylate 34.7 g of anhydrous $K_2CO_3$ (0.35 mol) was added to a solution of 64.2 g of ethyl 2-(3-cyano-2,4-dichloro-5-fluorobenzoyl)-3-cyclopropylaminoacrylate (0.173 mol) in 220 ml of DMF. The reacting mixture was stirred at 40–45° C. for 2.5 hours, and the reaction was monitored by TLC. The reactant was then poured into 800 ml of ice-water, filtered, washed with water (100 ml×2), and dried. The resultant solid was dissolved in 120 ml of 95% ethanol and then refluxed for 15 minutes, cooled, filtered and dried to afford 53.2 g of ethyl 8-cyano-1-cyclopropyl-7-chloro-6-fluoro-1,4-dihydro-4-oxo-3-quinolinecarboxylate (0.159 mol) as a white solid, mp 196–199° C., in 90.1% yield.

8-Cyano-1-cyclopropyl-7-chloro-6-fluoro-1,4-dihydro-4-oxo-3-quinolinecarboxylic Acid 29.4 g of ethyl 1-cyclopropyl-7-chloro-6-fluoro-8-methoxy-1,4-dihydro-4-oxo-3-quinolinecarboxylate (0.088 mol), 160 ml of acetate acid, 100 ml of water and 18 ml of concentrated sulfuric acid were stirred at 100–110° C. for 40 minutes. The resulting mixture was cooled and filtered. The precipitate was re-crystallized from chloroform-ethanol to give 23.8 g of 1-cyclopropyl-7-chloro-6-fluoro-8-methoxy-1,4-dihydro-4-oxo-3-quinolinecarboxylic acid (0.0775 mol) in 88.1% yield, mp 288–293° C.

EXAMPLE 3

Sparcarboxylic Acids Prepared From Pentafluoroacetylbenzene

Ethyl Pentafluorobenzoylacetate 71.4 g (0.34 mol) of pentafluoroacetylbenzene in 1000 ml of diethyl carbonate was stirred. 50.0 g (1.04 mol) of 50% NaH was added in batch to the resulting solution at ambient temperature. After the addition, the reaction was carried out at 80° C. for three hours. The reactant was then poured into ice-water containing a little amount of acetate acid. The resulting mixture was extracted with ethyl ether. The extract was washed with water, dried over anhydrous sodium sulfate. The residue of the solution was re-crystallized from methanol after ethyl ether was evaporated and excessive dimethyl carbonate was recovered from the solution. 80.5 g of ethyl pentafluorobenzoylacetate (112–121° C./8 Pa, 0.286 mol) was given under reduced pressure in 80.6% yield.

Ethyl 2-(Pentafluorobenzoyl)-3-cyclopropylaminoacrylate 70.5 g of ethyl pentafluorobenzoylacetate (0.25 mol), 66.6 g of triethyl orthoformate (0.45 mol) and 77.4 g of diacetyl oxide (0.72 mol) were stirred at 150° C. for 2.5 hours. Fractions having a lower boiling point were evaporated under reduced pressure. To the residue was added 250 ml of anhydrous ethanol. 14.5 g of cyclopropylamine (0.25 mol) was added to the solution under cooling of ice water and the reaction was then carried out at room temperature for 2 hours. The resultingt mixture was filtered under suction. The residue was re-crystallized from a mixture of petroleum ether and cyclohexane to yield 62.8 g (0.18 mol) of ethyl 2-(pentafluorobenzoyl)-3-cyclopropylaminoacrylate in 72.0% yield, mp 88–91° C.

Ethyl 1-Cyclopropyl-5,6,7,8-tetrafluoro-1,4-dihydro-4-oxo-3-quinolinecarboxylate 34.7 g of anhydrous $K_2CO_3$ was added to a solution of 60.4 g of ethyl 2-pentafluorobenzoyl-3-cyclopropylaminoacrylate (0.173 mol) in 220 ml of DMF. The reactants were stirred at 40–45° C. for 2.5 hours, and the reaction was monitored by TLC. The resulting mixture was then poured into 800 ml of ice-water, filtered, washed with water (100 ml×2), and dried. The resulting solid was dissolved in 120 ml of 95% methanol and then refluxed for 15 minutes, cooled, filtered and dried to give 53.0 g of ethyl 1-cyclopropyl-5,6,7,8-tetrafluoro-1,4-dihydro-4-oxo-3-quinolinecarboxylate (0.156 mol) as a white solid, mp 169–171° C., in 93% yield.

Ethyl 5-Benzylamino-1-cyclopropyl-6,7,8-trifluoro-1,4-dihydro-4-oxo-3-quinolinecarboxylate 53.0 g of ethyl 1-cyclopropyl-5,6,7,8-tetrafluoro-1,4-dihydro-4-oxo-3-quinolinecarboxylate (0161 mol), 15.4 ml of benzyl amine, and 37.0 g of anhydrous $K_2CO_3$ in 220 ml of acetonitrile were stirred at 100–110° C. for 1 hour. The reaction was monitored by TLC. After the solvent was evaporated, the residue was re-crystallized from ethanol to give 53.7 g of ethyl 1-cyclopropyl-6,7,8-trifluoro-1,4-dihydro-4-oxo-3-quinolinecarboxylate (0.129 mol) in 80.0% yield, mp 133–135° C.

Ethyl 5-Amino-1-cyclopropyl-6,7,8-trifluoro-1,4-dihydro-4-oxo-3-quinolinecarboxylate To a solution of 46.2 g of ethyl 5-benzylamino-1-cyclopropyl-6,7,8-trifluoro-1,4-dihydro-4-oxo-3-quinolinecarboxylate (0.111 mol) dissolved in a mixture of 200 ml of acetic acid and ethanol were added 0.5 g of 5% Pd/C catalyst. Hydrogen gas was introduced at room temperature and monitored with TLC. The reaction was carried out for around 3 hours. Precipitate collected by filtration was dissolved in chloroform and filtered to remove the catalyst. After removing the solvent by evaporation, the residue was crystallized from a mixture of chloroform and ethanol to give 32.4 g of ethyl 5-amino-1-cyclopropyl-6,7,8-trifluoro-1,4-dihydro-4-oxo-3-quinolinecarboxylate (0.0944 mol) in 85.0% yield, mp. 235–237° C.

Sparcarboxylic Acid: 5-Amino-1-cyclopropyl-6,7,8-trifluoro-1,4-dihydro-4-oxo-3-quinolinecarboxylic Acid 28.7 g of ethyl 5-amino-1-cyclopropyl-6,7,8-trifluoro-1,4-dihydro-4-oxo-3-quinolinecarboxylate (0.088 mol), 160 ml of acetic acid, and a mixture of 100 ml of water and 18 ml of concentrated sulfuric acid were stirred at 100–110° C. for 40 minutes. The reacting mixture was cooled and filtered. The precipitate was recrystallized from chloroform-ethanol to give 25.6 g 5-amino-1-cyclopropyl-6,7,8-trifluoro-1,4-dihydro-4-oxo-3-quinolinecarboxylic acid (Sparcarboxylic acid, 0.086 mol), mp. 293–295C., in 98.0% yield.

EXAMPLE 4

Sparcarboxylic Acids Prepared From 2,4,6-Trichloro-3,5-difluoroacetylbenzene

Ethyl 2,4,6-Trichloro-3,5-difluorobenzoylacetate 88.2 g of 2,4,6-trichloro-3,5-difluoroacetylbenzene (0.34 mol) in 1000 ml of diethyl carbonate was stirred. 50.0 g (1.04 mol) of 50% NaH was added in batch to the resulting solution at ambient temperature. After the addition, the reaction was carried out at 80° C. for 3 hours. The reactant was then poured into ice-water containing a little amount of acetate acid. The resulting mixture was extracted with ethyl ether. The extract was washed with water, dried over anhydrous sodium sulfate. The residue of the solution was re-crystallized from toluene, after ethyl ether was evaporated and excessive diethyl carbonate was recovered from the solution to give 93.3 g of ethyl 2,4,6-trichloro-3,5-fluorobenzoylacetate (0.276 mol) in 81.2% yield.

Ethyl 2-(2,4,6-Trichloro-3,5-difluorobenzoyl)-3-cyclopropylaminoacrylate 82.9 g of ethyl 2,4,6-trichloro-3,5-difluorobenzoylacetate (0.25 mol), 66.6 g of triethyl orthoformate (0.45 mol) and 77.4 g of diacetyl oxide (0.72 mol) were stirred at 150° C. for 2.5 hours. Fractions having a lower boiling point were evaporated under reduced pressure. To the residue was added 250 ml of anhydrous ethanol. 14.5 g of cyclopropylamine (0.25 mol) was added to the solution under cooling of ice water and the reaction was then carried at room temperature for 2 hours. The resultant mixture was filtered under suction. The residue was re-crystallized from a mixture of petroleum ether and cyclohexane to yield 74.5 g (0.187 mol) of ethyl 2-(2,4,6-trichloro-3,5-difluorobenzoyl)-3-cyclopropylaminoacrylate in 74.6% yield.

Ethyl 1-Cyclopropyl-5,7-dichloro-6,8-difluoro-1,4-dihydro-4-oxo-3-quinolinecarboxylate 34.7.0 g of anhydrous $K_2CO_3$ was added to a solution of 68.9 g of ethyl 2-(2,4,6-trichloro-3,5-difluorobenzoyl-3-cyclopropylaminoacrylate (0.173 mol) in 220 ml of DMF. The reacting mixture was stirred at 40–45° C. for 2.5 hours, and the reaction was monitored by TLC. The resultant was then poured into 800 ml of ice-water. The resulting mixture was filtered. The precipitate was washed with water (100 ml×2), and dried. The resulting solid was dissolved in 120 ml of 95% ethanol and then refluxed for 15 minutes. The resulting mixture was cooled, filtered and dried to give 60.4 g of ethyl 1-cyclopropyl-5,6,7,8-tetrafluoro-1,4-dihydro-4-oxo-3-quinolinecarboxylate (0.167 mol) as a white solid, mp 191–195° C., in 96.4% yield.

Ethyl 5-Benzylamino-1-cyclopropyl-7-chloro-6,8-difluoro-1,4-dihydro-4-oxo-3-quinolinecarboxylate 58.3 g of ethyl 1-cyclopropyl-5,7-dichloro-6,8-difluoro-1,4-dihydro-4-oxo-3-quinoline carboxylate (0161 mol), 15.4 ml of benzyl amine, and 37.0 g of anhydrous $K_2CO_3$ in 220 ml of acetonitrile were stirred at 100–110° C. for 1 hour. The reaction was monitored by TLC. After the solvent was evaporated, the residue was re-crystallized from ethanol to give 58.3 g of ethyl 1-cyclopropyl-7-chloro-6,8-difluoro-1,4-dihydro-4-oxo-3-quinolinecarboxylate (0.135 mol) in 83.7% yield.

Ethyl 5-Amino-1-cyclopropyl-7-chloro-6,8-difluoro-1,4-dihydro-4-oxo-3-quinolinecarboxylate To a solution of 48.0 g of ethyl 5-benzylamino-1-cyclopropyl-7-chloro-6,8-difluoro-1,4-dihydro-4-oxo-3-quinolinecarboxylate (0.111 mol) dissolved in a mixture of 200 ml of acetic acid and ethanol was added 0.5 g of 5% Pd/C catalyst. Hydrogen gas was introduced at room temperature. The reaction was monitored with TLC and carried out for around 3 hours. Precipitates collected by filtration were dissolved in chloroform and filtered to remove the catalyst. After removing the solvent by evaporation, the residue was recrystallized from a mixture of chloroform and ethanol to give 32.0 g of ethyl 5-amino-1-cyclopropyl-7-chloro-6,8-difluoro-1,4-dihydro-4-oxo-3-quinolinecarboxylate (0.093 mol) in 83.9% yield.

Sparcarboxylic Acid: 5-Amino-1-cyclopropyl-7-chloro-6,8-difluoro-1,4-dihydro-4-oxo-3-quinolinecarboxylic Acid 30.1 g of ethyl 5-amino-1-cyclopropyl-6,7,8-trifluoro-1,4-dihydro-4-oxo-3-quinolinecarboxylate (0.088 mol), 160 ml of acetic acid, and a mixture of 100 ml of water and 18 ml of concentrated sulfuric acid were stirred at 100–110° C. for 40 minutes. The reacting mixture was cooled and filtered. The precipitate was crystallized from chloroform-ethanol to give 26.8 g of 5-amino-1-cyclopropyl-7-chloro-6,8-difluoro-1,4-dihydro-4-oxo-3-quinolinecarboxylic acid (Sparcarboxylic acid, 0.0852 mol), mp. 283–287C., in 96.8% yield.

Preparation of Halogen Acetylbenzene

Example 5 Preparation of 2,4-Dichloro-5-fluoro-3-methoxyacetylbenzene a. Preparation of 2,4-Dichloro-5-fluoronitrobenzene 58.3 ml of 2,4-dichrolofluorobenzene (0.50 mol) was added to a mixture of 60 ml of concentrated nitric acid (1.41 mol), 93 ml of concentrated sulfuric acid (1.75 mol) and 16.5 ml of water. The reaction was carried out at 50–60° C. for 2 hours. The reactant was then poured into an ice-water, filtered, washed with water to be neutral and dried to yield 99.9 g of 2,4-dichloro-5-fluoronitrobenzene (0.476 mol) as a slightly yellow crystal, in 95.1% yield, mp 39–42° C.

b. Preparation of 3-Bromo-2,4-dichloro-5-fluoronitrobenzene 96.6 g of 2,4-dichloro-5-fluoronitrobenzene (0.46 mol) was stirred with 1150 ml of glacial acetate acid containing 9.7 ml of bromine. Then, a solution consisting of 690 ml of concentrated sulfuric acid and 464 ml of water was added thereto. To the resultant was added 67.5 g of potassium bromate seven times (9.65 g each) at 40° C. over around 2 hours. The reaction was ceased after 8 hours. The reacting mixture was slowly poured into 3000 ml of water containing 46.0 g of sodium bisulfite, and kept overnight. The resultant was filtered, and washed with warm water (about 30° C.) from three to four times, and dried to give a primrose crystal of 3-bromo-2,4-dichloro-5-fluoronitrobenzene, 122.1 g (0.423 mol), mp 51–53.5° C., in 91.9% yield.

c. Preparation of 2,4-Dichloro-5-fluoro-3-methoxylnitrobenzene 120 g of 3-bromo-2,4-dichloro-5-fluoronitrobenzene (0.415 mol), 1.66 g of NaOH (0.042 mol) and 26.9 g of sodium methoxide (0.498 mol) in 500 ml of methanol were stirred at 60° C. for 4 hours. The reactant was extracted with ethyl ether, washed successively with water, dilute hydrochloric acid solution, and water, dried over anhydrous sodium sulfate, and evaporated. The residue was recrystallized from ethanol to give 73.5 g of 2,4-dichloro-5-fluoro-3-methoxynitrobenzene (0.306 mol) in 73.8% yield.

d. Preparation of 2,4-Dichloro-5-fluoro-3-methoxyaniline 72.0 g of 2,4-dichloro-5-fluoro-3-methoxynitrobenzene (0.30 mol) and 2.65 g of Pd/C in 500 ml of methanol were hydrogenated under 3 Mpa (hydrogen pressure) at 60° C. for 3 hours. The reactant was cooled to room temperature. The catalyst was filtered out, and the solvent was evaporated to give 58.5 g of 2,4-dichloro-5-fluoro-3-methoxyaniline (0.279 mol) in 92.9% yield.

e. 2,4-Dichloro-5-fluoro-3-methoxybromobenzene

To 165 ml of a mixture of concentrated hydrochloric acid and water (1:1) was added 52.5 g of 2,4-dichloro-5-fluoro-3-methoxyaniline (0.25 mol). The resultant was stirred to be a slurry, and cooled to 0–5° C. Over 30 minutes, a solution of sodium nitrite (18.2 g) in water (50 ml) was added dropwise to the slurry. The resulting solution was added slowly to a solution of cuprous bromide (0.299 mol) and hydrobromic acid (160 ml). The reactant was stirred for 2 hours, and kept overnight. The resulting mixture was wet-distilled and the distilled materials were extracted with toluene. The oil layer was washed with 10% aqueous solution of NaOH, concentric sulfuric acid and water, dried over anhydrous sodium sulfate, and evaporated. The residue was purified by silica gel chromatography eluting with n-hexane-dichloromethane to give 58.1 g of 2,4-dichloro-5-fluoro-3-methoxybromobenzene (0.212 mol) in 84.9% yield.

f. Preparation of 2,4-Dichloro-5-fluoro-3-methoxyacetyl-benzene 0.20 mol of 2,4-dichloro-5-fluoro-3-methoxybromo-benzene, 0.22 mol of powder of magnesium, 0.24 mol of cuprous chloride in 240 ml of tetrahydrofuran were stirred at ambient temperature to initiate the reaction, and then quickly cooled to −30±10° C. The reaction was monitored by TLC to be finished. A solution of acetyl chloride (0.30 mol) in 50 ml of toluene was added dropwise to the resulting mixture. The reaction was carried out at −30±110° C. for 8 hours. The temperature of the reaction was then increased to room temperature and stirred for 3 hours. The reactant was poured into a mixture of 170 g of crushed ice containing 75 ml of 25% aqueous solution of sulfuric acid. The resulting mixture was stirred for 5 minutes. The organic phase was separated off. The aqueous layer was extracted by toluene. The combined organic phases were washed successively with aqueous solution of sodium chloride, aqueous solution of sodium bicarbonate and water, and dried over anhydrous sodium sulfate. The solvent was evaporated under reduced pressure. The residue was recrystallized from ethanol to afford 38.7 g of 2,4-dichloro-5-fluoro-3-methoxyacetyl-benzene (0.163 mol) in 81.6% yield, mp. 36.7–39.4° C.

EXAMPLE 6

Preparation of 3-Cyano-2,4-dichloro-5-fluoroacetylbenzene a. Preparation of 3-Cyano-2,4-dichloro-5-fluoronitro-benzene 120 g of 3-bromo-2,4-dichrolo-5-fluorobenzene (0.415 mol) as prepared in Example 5, 36.9 g of anhydrous cuprous cyanide (0.46 mol) and 200 ml of DMF were stirred under waterless atmosphere and heated to 100° C. for 6 hours. TLC monitored the reaction to the completion. The reactant was cooled to room temperature, and then added to a solution of iron trichloride (83 g), concentrated hydrochloric acid (5.5 ml) and 830 ml of water. The resulting mixture was stirred at 50–60° C. for 30 minutes. The reactant was extracted with ethyl ether. The organic layer was washed with brine and dried over anhydrous $MgSO_4$. After the solvent was evaporated off, the residue was purified by silicon gel chromatography eluting with toluene. The crude product was recrystallized from methanol to yield 58.5 g of 3-cyano-2,4-dichloro-5-fluoronitrobenzene (0.249 mol) in 60.0% yeild.

b. Preparation of 3-Cyano-2,4-dichloro-5-fluoroaniline 27.0 g of 3-cyano-2,4-dichloro-5-fluoronitrobenzene (0.247 mol), 500 ml of ethanol and 2.18 g of Pd/C were heated to 60° C. and hydrogenated under 3 Mpa of hydrogen pressure for 3 hours. The reaction mixture was cooled to room temperature. The catalyst was filtered off. After removing the solvent, 48.0 g of 3-cyano-2,4-dichloro-5-fluoroaniline were given in 94.7 yield.

c. Preparation of 3-Cyano-2,4-dichloro-5-fluorobromo-benzene 47.2 g of 3-cyano-2,4-dichloro-5-fluoroaniline (0.23 mol) were added to a solution of 150 ml of hydrochloric acid-water (1:1). The resulting mixture was stirred to be a slurry and then cooled to 0–5° C. A solution of sodium nitrite (16.7 g, 0.242 mol) and water (46 ml) was added thereto over 30 minutes. The resulting solution was added to a solution of cuprous bromide (0.275 mol) in 147 ml of hydrobromic acid. The reaction mixture was stirred for 2 hours and allowed overnight. The resulting mixture was wet-distilled. The distilled fraction was extracted with toluence. The oil layer was washed successively with 10% aqueous solution of NaOH, concentrated sulfuric acid and water, and dried over anhydrous sodium sulfate. After removing the solvent, the residue was crystallized from toluene to give 53.3 g of 3-cyano-2,4-dichloro-5-fluorobromobenzene (0.198 mol) in 86.2% yield.

d. Preparation of 3-Cynao-2,4-dichloro-5-fluoroacteyl-benzene 0.18 mol of 3-cyano-2,4-dichloro-5-fluorobromobenzene, powder of magnesium (0.198 mol), cuprous chloride (0.216 mol) and 216 ml of THF were stirred to initiate the reaction at room temperature. The reaction then was quickly cooled to −30±10° C. TLC was used to monitored the reaction to the completion. Then, to the reaction mixture was added 21.2 g of acetyl chloride (0.27 mol) in 45 ml of toluene. The reaction was carried out at −30±10° C. for 8 hours. The reaction was then heated to room temperature and stirred for 3 hours. The reactant was then poured into 150 g of crushed ice containing 75 ml of 25% sulfuric acid solution and stirred for 5 minutes. The organic layer was separated. The aqueous layer was extracted with toluene. The combined organic layers were washed with aqueous solution of NaCl, aqueous solution of $NaHCO_3$ and water, and dried over anhydrous sodium sulfate. The solvent was evaporated under reduced pressure. The residue was crystallized form ethanol to give 0.148 mol of 3-cynao-2,4-dichloro-5-fluoroacteylbenzene in 82.3% yield, mp. 94.3–96.0° C.

EXAMPLE 7

2,4,6-Trichloro-3,5-difluoroacetylbenzene a. Preparation of 3,5-Dichloro-2,4-dichloronitrobenzene 100 ml of tetrachloro methane and 30.2 g of 2,4-difluoronitrobenzene (0.19 mol) were introduced a three-necked flash equipped with a reflux condenser, a thermometer and a stirrer. Chlorine gas was introduced under reflux for about three hours and the reaction was monitored by TLC. After the reaction was finished, terachloromethane was evaporated and the residue was recrystallized from ethyl acetate to give 39.0 g of 3,5-dichloro-2,4-dichloronitrobenzene (0.171 mol) in 90.0% yield, m.p. 41–44° C.

b. Preparation of 3,5-Dichloro-2,4-difluoroaniline 38.5 g of 3,5-difluoro-2,4-difluoronitrobenzene (0.169 mol) and 1.49 g of Pd/C were introduced into a 100 ml autoclave. Hydrogen gas was introduced into the autoclave under 3 Mpa of hydrogen pressure at 60° C. for three hours. The reactant was cooled to room temperature. The catalyst was filtered off, and the resulting mixture was distilled to give 31.8 g of 3,5-dichloro-2,4-difluoroaniline (0.161 mol) in 95.1% yield.

c. Preparation of 2,4-Difluoro-1,3,5-trichlorobenzene 31.1 g of 3,5-dichloro-2,4-difluoroaniline (0.157 mol) was added to 100 ml of a solution of concentrated hydrochloric acid and water (1:1) at 70° C. The resulting mixture was stirred to be a slurry and cooled to 0–5° C. To the mixture was added 11.6 g of aqueous solution of sodium nitrite (0.165 mol) over 30 minutes. The resulting solution was added to a solution of CuCl (0.188 mol) and hydrochloric acid (100 ml). The reaction mixture was stirred for 2 hours and kept overnight. Fractions obtained by wet-distillation were extracted with toluene. The extract was washed successively with 10% aqueous solution of NaOH, concentrated sulfuric acid and water, dried over sodium sulfate and evaporated. The residue was recrystallized from toluene to give 27.7 g of 2,4-difluoro-1,3,5-trichlorobenzene (0.127 mol) in 81.1% yield.

d. Preparation of 2,4,6-Trichloro-3,5-difluorobromobenzene

A solution of 186 ml of concentrated sulfuric acid and 125 ml of water was slowly added to 27 g of 2,4-difluoro-1,3, 5-trichlorobenzene (0.124 mol) and 310 ml of glacial acetic acid containing 2.6 ml of bromine in a reaction flash under agitation. 18.2 g of $KBrO_3$ was added to the flash in 7 times (2.6 g each, around 1 hour) at 45° C. under agitation. The reaction was ceased after 8 hours. The reaction materials were poured into 1,000 ml of aqueous solution of $NaHSO_3$ (12.4 g) and kept overnight. The resulting mixture was filtered. The precipitate was washed with warm water 3–4 times, and dried to give 34.1 g of 2,4,6-trichloro-3,5-difluorobenzene (0.115 mol) in 92.9% yield.

e. Preparation of 2,4,6-Trichloro-3.5-difluoroacetylbenzene 0.1 mol of 3,5-difluoro-2,4,6-trichlorobromobenzene, powder of magnesium (0.11 mol), cuprous chloride (0.12 mol) in 120 ml of THF were stirred at room temperature until the reaction mixture appeared black, which showed the reaction had been initiated. The reaction then was quickly cooled to −30±10° C. GLC was used to monitored the reaction to the completion. Then, to the reaction mixture was added dropwise 11.78 g of acetyl chloride (0.27 mol) in 25 ml of toluene. The reaction was carried out at −30±10° C. for 8 hours. The reaction was then heated to room temperature and stirred for 3 hours. The reactant was poured into 150 g of crushed ice containing 75 ml of 25% sulfuric acid solution and stirred for 5 minutes. The organic layer was separated. The aqueous layer was extracted with toluene. The combined organic layers were washed with aqueous solution (45 ml) of NaCl, aqueous solution (44 ml) of $NaHCO_3$, water (45 ml) and saturated aquoues solution (25 ml) of NaCl, and dried over anhydrous sodium sulfate. The solvent was evaporated under reduced pressure. The residue was recrystallized form ethanol to give 0.0819 mol of 3,5-difluoro-2, 4,6-trichloroacteylbenzene in 81.9% yield, mp. 73–76° C.

What is claimed is:

1. A process for preparing quinolonecarboxylic acid derivatives having the formula (I):

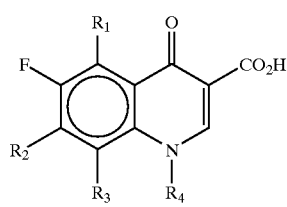

(I)

wherein $R_1$ is H, halogen, or amino, $R_2$ is halogen, $R_3$ is H, halogen, $C_{1-4}$ alkoxyl, or CN, $R_4$ is selected from the group consisting of $C_{3-6}$cycloalkyl, $C_{1-4}$alkyl, $C_{1-4}$alkoxy$C_{1-4}$alkyl, and $C_{1-4}$alkylamino$C_{1-4}$alkyl, comprising the steps of:

i) reacting a compound of the formula (II)

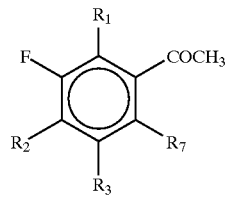

(II)

wherein $R_1$, $R_2$ and $R_3$ are defined as above, and $R_7$ is a halogen, with an alkyl carbonate to obtain a compound of the formula (III),

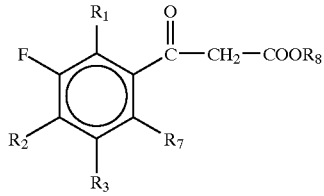

(III)

wherein $R_8$ is methyl or ethyl;

ii) reacting a compound of the formula (III) successively with an alkyl orthoformate and a compound of the formula (IV) $R_4NH_2$ to obtain a compound of the formula (V),

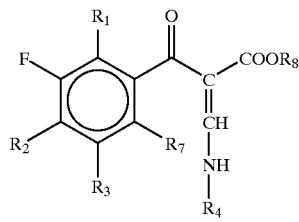

(V)

iii) cyclizing the compound of the formula (V) in the presence of a base to form a compound of the formula (VI); and

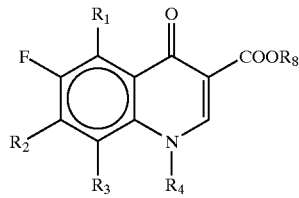

(VI)

iv) hydrolyzing the compound of the formula (VI) to obtain a compound of the formula (I).

2. A process according to claim 1, wherein $R_1$ is selected form the group consisting of H, F, Cl, and $NH_2$; $R_2$ is Cl or F; $R_3$ is selected from the group consisting of F, Cl, CN, and $C_{1-4}$alkoxy; and $R_4$ is a group selected from $C_{3-6}$cycloalkyl.

3. A process according to claim 2, where $R_3$ is F, CN or $OCH_3$; and $R_4$ is a group selected from $C_{3-6}$cylcoalkyl.

4. A process according to claim 3, wherein $R_1$ is H, F, or $NH_2$; $R_2$ is F; and $R_4$ is cyclopropyl or cyclohexyl.

5. A process according to claim 1 further comprising in step iv) converting a compound of the formula (I) in which $R_1$ is halogen to that in which $R_1$ is amino.

* * * * *